United States Patent [19]

Haag et al.

[11] 4,016,218

[45] Apr. 5, 1977

[54] ALKYLATION IN PRESENCE OF THERMALLY MODIFIED CRYSTALLINE ALUMINOSILICATE CATALYST

[75] Inventors: Werner O. Haag, Trenton; David H. Olson, Pennington, both of N.J.

[73] Assignee: Mobil Oil Corporation, New York, N.Y.

[22] Filed: May 29, 1975

[21] Appl. No.: 582,025

[52] U.S. Cl. .................. 260/671 R; 260/671 C
[51] Int. Cl.$^2$ .................................. C07C 3/52
[58] Field of Search ............... 260/671 R, 671 C

[56] References Cited
UNITED STATES PATENTS

| 3,751,504 | 8/1973 | Keown et al. | 260/671 R |
| 3,751,506 | 8/1973 | Burress | 260/671 C |
| 3,890,218 | 6/1975 | Morrison | 252/455 Z |

*Primary Examiner*—C. Davis
*Attorney, Agent, or Firm*—Charles A. Huggett; Raymond W. Barclay

[57] ABSTRACT

Process for the alkylation of aromatic hydrocarbons by contacting same with an olefin alkylating agent in a reaction zone maintained under conditions such that said alkylation is accomplished in the presence of a catalyst comprising a crystalline aluminosilicate zeolite, said zeolite having a silica to alumina ratio of at least about 12 and a constraint index, as hereinafter defined, within the approximate range of 1 to 12, said catalyst having been modified by prior thermal treatment to reduce the activity thereof, as determined by an alpha value, as described herein, to less than about 250 and preferably within the range of less than about 200 but greater than 10.

16 Claims, No Drawings

ALKYLATION IN PRESENCE OF THERMALLY MODIFIED CRYSTALLINE ALUMINOSILICATE CATALYST

BACKGROUND OF THE INVENTION

1. Field of the Invention

This invention relates to a process for the alkylation of an aromatic hydrocarbon by reaction with an olefin in the presence of a crystalline aluminosilicate catalyst which has undergone prior modification by subjection to a thermal treatment.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes liquid phase alkylation in the presence of X- or Y-type crystalline aluminosilicate zeolites, specifically such type zeolites wherein the cation is rare earth and/or hydrogen. U.S. Pat. No. 3,751,504 to Keown et al., and U.S. Pat. No. 3,751,506 to Burress describe vapor phase alkylation of aromatic hydrocarbons with olefins, e.g. benzene wth ethylene, in the presence of a ZSM-5 type zeolite catalyst.

While the latter type catalysts represent a distinct improvement over previously suggested crystalline aluminosilicate catalysts particularly with respect to improved aging properties, they have the disadvantage of producing unwanted quantities of impurities along with the desired alkyl aromatic product, thereby decreasing the overall yield and selectivity for such product.

Thus, in the alkylation of benzene with ethylene, while desired ethylbenzene is the major product, small amounts of di- and possibly triethylbenzenes are always produced simultaneously with ethylbenzene, such amounts depending on the conversion of benzene to ethylbenzene. The polyethylbenzenes formed can be recycled to the alkylation zone, where they undergo transalkylation with benzene to produce more ethylbenzene. Alternatively, the polyethylbenzenes can be transalkylated with benzene in a separate reactor. The formation of polyethylbenzenes hence does not constitute an ultimate loss of the alkylating agent, ethylene. On the other hand, aromatic compounds other than ethyl- and polyethylbenzenes, that are formed during the alkylation reaction, generally referred to as by-products, result in an irreversible loss of ethylene and cause difficulties in the product purification. By-products produced during ethylation of benzene include, for example, toluene, xylenes, cumene, n-propylbenzene, ethyltoluene, butylbenzene and other $C_{10}+$ aromatics, the majority being $C_7$-$C_9$ aromatics. The formation of these by-products is increased when the benzene conversion to ethylbenzene is high. Due to the high exothermicity of the alkylation reaction, ethylbenzene synthesis is generally carried out in a multiplicity of reactors with interstage cooling and addition of ethylene to the various stages, the ethylbenzene concentration increasing in subsequent stages. Undesired by-products are accordingly formed in increasing amounts in the latter stages of the process.

SUMMARY OF THE INVENTION

In accordance with the present invention, there has been discovered a process for improving the selectivity for the desired alkyl aromatic product, i.e. decreasing the formation of unwanted impurities while simultaneously improving the aging characteristics of the catalyst to afford a high yield of the alkylate of interest over a long commercially attractive period of time.

The process comprises effecting alkylation of aromatic hydrocarbons by contacting the same with an olefin under conditions effective for accomplishing said alkylation including a reactor inlet temperature between about 575° F. and 900° F., with a reactor bed temperature as much as 250° F. above the reactor inlet temperature, a pressure between atmospheric and 3000 psig, employing a mole ratio of aromatic hydrocarbon to olefin alkylating agent in the approximate range of 1:1 to 30:1 and a total feed weight hourly space velocity between about 2 and about 2000, in the presence of a catalyst comprising a crystalline aluminosilicate zeolite, said zeolite having a silica to alumina ratio of at least about 12, a constraint index of from 1 to 12 and which has been modified by prior thermal treatment thereof to control the activity, as determined by alpha value, below 250.

DESCRIPTION OF SPECIFIC EMBODIMENTS

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ration of at least about 12; and a structure providing constrained access to the crystalline free space.

The silica to alumina ration referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit hydrophobic properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly spaced velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| Synthetic Mordenite | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is aproximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed Nov. 29, 1974, and now abandoned. This zeolite can be identified, in terms of mole ratios of oxides and in the anhydrous state, as follows:

$(0.3-2.5)R_2O : (0-0.8)M_2O : Al_2O_3 : > 8 SiO_2$ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$(0.4-2.5)R_2O : (0-0.6) M_2O : Al_2O_3 : xSiO_2$ wherein R is an organic nitrogen-containing cation derived from a 2-(hydroxyalkyl)trialkylammonium compound, wherein alkyl is methyl, ethyl or a combination thereof, M is an alkali metal, especially sodium, and $x$ is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 5.0 ± 0.10 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻is calculated only from the inorganic sources of alkali without any organic base contribution). Thereafter, the crystals are separated from the liquid and recovered. Typical reaction conditions consist of heating the foregoing reaction mixture to a temperature of from about 90° F. to about 400° F. for a period of time of from about 6 hours to about 100 days. A more preferred temperature range is from about 150° F. to about 400° F. with the amount of time at a temperature in such range being from about 6 hours to about 80days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours ZSM-35 is more particularly described in U.S. Application Ser. No. 528,061, filed Nov. 29, 1974. This zeolite can be identified, in terms of mole ratios of oxides and in the anhydrous state, as follows:

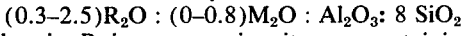
(0.3–2.5)R₂O : (0–0.8)M₂O : Al₂O₃: 8 SiO₂ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

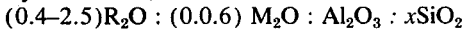
(0.4–2.5)R₂O : (0.0.6) M₂O : Al₂O₃ : xSiO₂ wherein R is an organic nitrogen-containing cation derived from ethylenediamine or pyrrolidine, M is an alkali metal, especially sodium, and $x$ is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong- Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 35 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° F. to about 400° F. for a period of time of from about 6 hours to about 100 days. A more preferred temperature range is from about 150° F. to about 400° F. with the amount of time at a temperature in such range being from about 6 hours to about 80 days.

The digestion of the gel particles is carried out until cyrstals form. The solid product is separated from the reaction medium, as by cooling the whole to room temperature, filtering and water washing. The crystalline product is dried, e.g. at 230° F., for from about 8 to 24 hours.

The specific zeolites described when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, silbite, dachiardite, epistilbite, heulandite, and clinoptilalite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are the most desired. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally be intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal, and characterized by an alpha value hereinafter described, are then subjected to thermal treatment, preferably in the presence of steam, to reduce the activity thereof, as expressed in terms of alpha value, as described herein, to less than about 250 and preferably in the range of less than about 200 but greater than 10.

The alpha value reflects the relative activity of the catalyst with respect to a high activity silica-alumina cracking catalyst. To determine the alpha value as such term is used herein, n-hexane conversion is determined at about 800° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and the remainder $SiO_2$. This method of determining alpha, modified as described above, is more fully described in the Journal of Catalysis, Vol. VI, pages 278–287, 1966.

Thermal treatment will depend on the nature of the atmosphere to which the zeolite is exposed. When such atmosphere is an inert gas, the minimum effective temperature will be about 1200° F. and may extend up to 1800° F. When the treating atmosphere is steam, lower temperatures may be used extending from about 500° F. to about 1800° F. depending on the steam pressure, with the use of higher pressure requiring a lower temperature. This treatment is carried on for a period of time sufficient to effect the desired reduction in alpha. Generally, such period will be between about 1/2 hour and 100 hours. Such thermal treatment can be carried out in any inert atmosphere such as air, nitrogen, carbon dioxide, carbon monoxide, hydrogen, flue gas, argon, methane, helium, oxygen and suitable mixtures thereof, but is preferably effected in an atmosphere containing steam. A steam treating atmosphere may be employed which is 100 percent steam or steam admixed with a gas which is substantially inert with respect to the zeolite. It is contemplated that the thermal treatment will generally be effected at atmospheric pressure but pressures ranging from sub-atmospheric to several hundred atmospheres may be employed. With the use of elevated pressure, temperatures in the lower region of the above-specified range will usually be applicable in achieving the desired reduction in alpha value of the zeolite under treatment. Thus, it has been found, that at elevated steam pressure, the temperature of treatment can be reduced substantially to achieve the same degree of modification.

The crystalline aluminosilicate zeolites utilized herein generally have an activity, in terms of alpha, of greater than 400 and usually within the range of 500 to 10,000. It will be realized that extent of reduction in alpha value of such zeolites will depend on the severity and duration of the thermal treatment. Thus, substantially identical reduction in activity can be obtained utilizing a relatively short steam treatment under conditions of high temperature or a comparatively longer period of steam treatment at lower temperature. Illustrative of such situation is the finding that steaming of an extrudate of 65 weight percent HZSM-5 and 35 weight percent alumina for 2.5 hours at 1000° F. and 1 atmosphere pressure and steaming of a second sample of such extrudate for 72 hours at 650° F. and 33 atmospheres pressure both afforded a product having a reduced activity of about 120 in terms of alpha value.

Prior to use, the resulting modified zeolite may be dried in an inert atmosphere, e.g. air. Drying takes place at a temperature in the approximate range of 600° F. to 1050° F. and preferably between about 800° F. and 1000° F.

In practicing the desired alkylation process it may be desirable to incorporate the modified zeolite in another material resistant to the temperatures and other conditions employed in the alkylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

Exemplary of the hydrocarbons which may be alkylated by the process of this invention are aromatic compounds such as benzenes, naphthalenes, anthracenes, and the like and substituted derivatives thereof; and alkyl substituted aromatics, e.g. toluene, xylene and homologs thereof.

In accordance with this invention the alkylating agents employed are olefinic hydrocarbons having from 2 to 20 carbon atoms such as ethylene, propylene, and dodecylene.

Operating conditions employed in the process of the present invention are critical and will be dependent, at least in part, on the specific alkylation reaction being effected. Such conditions as temperature, pressure, space velocity and molar ratio of the reactants and the presence of inert diluents will have important affects on the process. Accordingly, the manner in which these conditions affect not only the conversion and distribution of the resulting alkylated products but also the rate of deactivation of the catalyst will be described below.

The process of this invention is conducted such that alkylation of an aromatic hydrocarbon compound, exemplified by benzene, with an alkylating agent, i.e. an olefinic hydrocarbon exemplified by ethylene, is carried out by contact in a reaction zone, such as, for example, a fixed bed of catalyst, uner alkylation effective conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline aluminosilicate zeolite, above-described, will be occupied by hydrogen ions. The alkylatable aromatic compound and olefinic hydrocarbon are desirably fed to a first stage at an appropriate mole ratio of one to the other. The feed to such first stage is heated. After some reaction takes place, such as, for example, when about 80% of the olefinic hydrocarbon is consumed. The effluent of the first stage is cooled to remove heat of reaction and more olefinic hydrocarbon is added (second stage) to maintain the mole ratio of aromatic compound to olefinic hydrocarbon within the range established for the first stage. A plurality of reaction stages are possible for the process of this invention. It is generally desirable to provide cooling between reactor stages.

Considering vapor-phase alkylation of benzene with ethylene, the first stage mole ratio of benzene to ethylene may be in the range of about 1:1 to about 30:1. The first stage feed is heated to a reactor inlet temperature within the range of about 575° F. to about 900° F. at a pressure within the range of about atmospheric to about 3000 psig. Preferred inlet temperatures fall within the range of about 600° F. to about 850° F. and preferred pressures fall within the range of about 25 psig to about 450 psig. The repeating of reaction staging is carried out while maintaining an overall aromatic hydrocarbon, e.g. benzene, to alkylating agent, e.g. ethylene, mole ratio of about 1:1 to about 30:1, with a preferred range of about 2.5:1 to about 25:1.

It is noted that extremely high total feed space velocities are possible in the process of this invention, i.e. up to 2000 lb. total feed/hr.-lb. crystalline aluminosilicate. An important factor in the present process is, however, the weight hourly space velocity (WHSV) of the alkylating agent, e.g. ethylene. The alkylating agent WHSV to each of any alkylation reactor stages is maintained between about 1 and about 10 lb. alkylating agent/hr.-lb. crystalline aluminosilicate. For the most desirable alkylating agent, i.e. ethylene, WHSV is within the range of about 2 to about 8 lb. ethylene/hr.-lb. crystalline aluminosilicate. When the ethylene WHSV is maintained within the above limits, an economical cycle between regeneration of catalyst exists.

The process of this invention may be carried out as a batch-type, semi-continuous or continuous operation utilizing a fixed or moving bed catalyst system. A preferred embodiment entails use of a fluidized catalyst zone wherein the reactants, e.g. benzene and ethylene, are passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the benzene and ethylene reactants.

The following examples will serve to illustrate the process of this invention without limiting the same:

EXAMPLE 1

A sample of HZSM-5 catalyst containing 65 percent HZSM-5 and 35 percent alumina binder was heated for six hours at 1000° F. in an inert atmosphere made up of 90 volume percent nitrogen and 10 volume percent of air. This material had an alpha value, as described herein, of 750.

EXAMPLE 2

A sample of HZSM-5 catalyst identical to the product prepared as in EXAMPLE 1 was modified by heating at a temperature of 1000° F. for 2.5 hours in an atmosphere of 100 percent steam at atmospheric pressure. The resulting material had an alpha value, as described herein, of 120.

EXAMPLE 3

Synthesis of ethylbenzene by ethylation of benzene was carried out in a fixed bed flow reactor by placing 0.5 gram of HZSM-5 catalyst treated as in Example 1 in a stainless steel reactor mounted vertically inside an electrical furnace. Benzene containing 14.98 weight percent ethylbenzene and 0.03 weight percent toluene and ethylene were passed downflow through the reactor at a pressure of 260 psig and a reactor temperature of 822°±2° F. The flow rate of the aromatic mixture was 74 ml. liquid/hour and that of the ethylene was 40 ml./minute measured as gas at atmospheric pressure and room temperature. These amounts correspond to a mole ratio of total aromatics to ethylene of 12. The liquid product was analyzed by gas chromatography.

EXAMPLE 4

Synthesis of ethylbenzene was carried out under conditions identical to those of EXAMPLE 3 except that 0.5 gram of HZSM-5 catalyst modified as in Example 2 was used.

The comparative results of EXAMPLES 3 and 4 are shown below in Table III.

TABLE III

| Catalyst of Example | 1 | 2 |
|---|---|---|
| Product Compositon, wt. % | | |
| Benzene | 71.97 | 70.92 |
| Toluene | 0.20 | 0.04 |
| Ethylbenzene | 25.09 | 25.54 |
| Xylenes | 0.13 | 0 |
| $C_9$-Aromatics | 0.16 | 0.06 |
| Diethylbenzene | 2.45 | 3.41 |
| Net Yield per Pass, wt. % | | |
| Alkylation products[a] | 12.56 | 13.97 |
| By-products[b] | 0.46 | 0.07 |
| Selectivity, wt. % | | |
| Alkylation products | 96.5 | 99.5 |
| By-products | 3.5 | 0.5 |
| | 100.00 | 100.0 |

[a] Ethylbenzene + diethylbenzene
[b] Toluene, xylenes and $C_9$-aromatics

It will be evident from the above results that the catalyst of Example 2, exemplary of that used in the process of the invention, produced an appreciably higher yield of alkylation product and significantly less byproducts. The alkylation selectivity for the catalyst of Example 2 was 99.5% compared to 96.5% for the catalyst of Example 1.

EXAMPLE 5

Synthesis of ethylbenzene was carried in the manner of Example 3 but at lower temperature and flow rate. The experimental conditions and the results are set forth below in Table IV.

TABLE IV

| Catalyst of Example | 1 | 2 |
|---|---|---|
| Temperature, °F. | 806 | 817 |
| Ethylene Feed Rate (cc/min)[a] | 15 | 15 |
| Liquid Feed Rate (cc/hr) | 37 | 32 |
| Product Composition, wt. % | | |
| Benzene | 77.76 | 77.38 |
| Toluene | 0.13 | 0.03 |
| Ethylbenzene | 20.59 | 21.07 |
| Xylenes | 0.08 | n.d.[d] |
| C₉-Aromatics | 0.19 | n.d.[d] |
| Diethylbenzene | 1.16 | 1.40 |
| New Yield per Pass, wt. % | | |
| Alkylation products[b] | 6.77 | 7.49 |
| By-products[c] | 0.37 | n.d.[d] |
| Selectivity | | |
| Alkylation products | 95.4 | 100 |
| By-products | 4.6 | — |
| | 100.0 | 100 |

[a]Measured at ambient conditions
[b]Ethylbenzene + diethylbenzene
[c]Toluene, xylenes and C₉-aromatics
[d]Not detectable, present in less than 0.01%

From the above results, the performance advantages of the catalyst used in the process of the invention, exemplified by the catalyst of Example 2, are clearly demonstrated, e.g. a higher yield of alkylation product with no observable by-product formation.

EXAMPLE 6

A sample of HZSM-5 catalyst, identical to the product prepared as in Example 1, was heated in a stream of dry air at various temperatures for 3 hours. The resulting material had alpha values as follows:

| Temperature of Heating | Alpha |
|---|---|
| 1600° F. | 250 |
| 1700° F. | 200 |
| 1800° F. | 54 |

It is to be understood that the foregoing description is merely illustrative of preferred embodiments of the invention of which many variations may be made by those skilled in the art within the scope of the following claims without departing from the spirit thereof.

We claim:

1. A process for effecting alkylation of an aromatic hydrocarbon charge which comprises contacting said aromatic hydrocarbon charge with an olefinic hydrocarbon alkylating agent under conditions effective for accomplishing said alkylation including a reactor inlet temperature between about 575° F. and about 900° F., a reactor pressure between atmospheric and about 3000 psig, employing a mole ratio of hydrocarbon aromatic charge to olefinic hydrocarbon alkylating agent in the approximate range of 1:1 to 30:1 and a total weight hourly space velocity between about 2 and 2000 in the presence of a catalyst comprising a crystalline aluminosilicate zeolite, having more than 50 percent of the cationic sites thereof occupied by hydrogen ions, said zeolite having a silica to alumina ratio of at least about 12, a constraint index within the approximate range of 1 to 12, said catalyst having been modified by prior thermal treatment at about 1200° F. to about 1800° F. in an inert atmosphere or at about 500° F. to about 1800° F. in steam to reduce the alpha value thereof to less than about 250.

2. The process of claim 1 wherein said alkylating agent is an olefinic hydrocarbon containing from 2 to 20 carbon atoms.

3. The process of claim 1 wherein said crystalline aluminosilicate zeolite is characterized by a silica/alumina ratio in excess of 30.

4. The process of claim 1 wherein said crystalline zeolite is ZSM-5.

5. The process of claim 1 wherein said alpha value is within the range of less than about 200 but greater than 10.

6. The process of claim 1 wherein the crystalline aluminosilicate zeolite is combined in an amount between about 1 and about 99 weight percent in a binder therefor.

7. The process of claim 6 wherein said binder is alumina.

8. The process of claim 1 wherein said alkylation is effected in the vapor phase, said aromatic hydrocarbon is benzene and wherein said olefinic hydrocarbon alkylating agent is ethylene.

9. The process of claim 8 wherein the reactor temperature is between about 600° F. and about 850° F. and the reaction is between about 25 and about 450 psig.

10. The process of claim 8 wherein said crystalline aluminosilicate zeolite is ZSM-5.

11. The process of claim 8 wherein the crystalline aluminosilicate zeolite is combined in an amount between about 1 and about 99 weight percent in a binder thereof.

12. The process of claim 11 wherein said binder is alumina.

13. The process of claim 1 wherein said thermal treatment is effected in the presence of steam.

14. The process of claim 4 wherein said thermal treatment is effected in the presence of steam.

15. The process of claim 8 wherein said thermal treatment is effected in the presence of steam.

16. The process of claim 1 wherein the catalyst consists essentially of the hydrogen form of said crystalline aluminosilicate zeolite.

* * * * *